United States Patent
Lee et al.

(10) Patent No.: US 12,036,389 B2
(45) Date of Patent: Jul. 16, 2024

(54) PREDICTION OF MEAL AND/OR EXERCISE EVENTS BASED ON PERSISTENT RESIDUALS

(71) Applicant: Insulet Corporation, Acton, MA (US)

(72) Inventors: Joon Bok Lee, Acton, MA (US); Yibin Zheng, Hartland, WI (US); Jason O'Connor, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 378 days.

(21) Appl. No.: 17/142,425

(22) Filed: Jan. 6, 2021

(65) Prior Publication Data

US 2021/0205535 A1 Jul. 8, 2021

Related U.S. Application Data

(60) Provisional application No. 62/957,620, filed on Jan. 6, 2020.

(51) Int. Cl.
*A61M 5/172* (2006.01)
*A61M 5/142* (2006.01)

(52) U.S. Cl.
CPC ...... *A61M 5/1723* (2013.01); *A61M 5/14244* (2013.01); *A61M 2205/52* (2013.01); *A61M 2230/201* (2013.01)

(58) Field of Classification Search
CPC ............ A61M 5/1723; A61M 5/14244; A61M 2205/52; A61M 5/142; A61M 5/14248;
(Continued)

(56) References Cited

U.S. PATENT DOCUMENTS

| 303,013 A | 8/1884 | Horton |
| 2,797,149 A | 6/1957 | Skeggs |

(Continued)

FOREIGN PATENT DOCUMENTS

| AU | 2015200834 A1 | 3/2015 |
| AU | 2015301146 A1 | 3/2017 |

(Continued)

OTHER PUBLICATIONS

US 5,954,699 A, 09/1999, Jost et al. (withdrawn)
(Continued)

*Primary Examiner* — Kami A Bosworth
*Assistant Examiner* — Avery Smale
(74) *Attorney, Agent, or Firm* — GOODWIN PROCTER LLP

(57) ABSTRACT

Exemplary embodiments provide an approach to predicting meal and/or exercise events for an insulin delivery system that otherwise does not otherwise identify such events. The insulin delivery system may use a model of glucose insulin interactions that projects estimated future glucose values based on a history of glucose values and insulin deliveries for a user. The predictions of meal events and/or exercise events may be based on residuals between actual glucose values and predicted glucose values. The exemplary embodiments may calculate a rate of change of the residuals over a period of time and compare the rate of change to thresholds to determine whether there likely has been a meal event or an exercise event. The insulin delivery system may then take measures to account for the meal event or the exercise event by the user.

11 Claims, 10 Drawing Sheets

(58) Field of Classification Search
CPC ........ A61M 2005/14272; A61M 5/168; A61M 5/16804; A61M 5/16877; A61M 5/172; A61M 2005/1726; A61M 2205/33; A61M 2205/3303; A61M 2205/3334; A61M 2230/201; G16H 20/17

See application file for complete search history.

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |

(56) References Cited

U.S. PATENT DOCUMENTS

| | | |
|---|---|---|
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B2 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |

(56) References Cited

U.S. PATENT DOCUMENTS

| | | |
|---|---|---|
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | L. Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0183060 A1* | 7/2008 | Steil ............... A61B 5/4839 606/151 |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |

(56) References Cited

U.S. PATENT DOCUMENTS

| | | |
|---|---|---|
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | O'Connor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 0801578 B1 | 7/2006 |
| EP | 1281351 B1 | 5/2008 |
| EP | 2666520 A1 | 10/2009 |
| EP | 2139382 A1 | 1/2010 |
| EP | 2397181 A1 | 12/2011 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 1571582 B1 | 4/2019 |

(56) References Cited

FOREIGN PATENT DOCUMENTS

| | | |
|---|---|---|
| EP | 2897071 B1 | 5/2019 |
| EP | 3607985 A1 | 2/2020 |
| EP | 2992826 B1 | 1/2023 |
| GB | 2443261 A | 4/2008 |
| JP | 51125993 A | 11/1976 |
| JP | 02131777 A | 5/1990 |
| JP | 2006175227 A | 7/2006 |
| JP | 2004283378 A | 10/2007 |
| JP | 2008545493 A | 12/2008 |
| JP | 2010523167 A | 7/2010 |
| JP | 2017127653 A | 7/2017 |
| JP | 2017525451 A | 9/2017 |
| JP | 2018153569 A | 10/2018 |
| JP | 2019525276 A | 9/2019 |
| JP | 2019530489 A | 10/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 2004043250 A1 | 5/2004 |
| WO | 04092715 A1 | 10/2004 |
| WO | 2005051170 A2 | 6/2005 |
| WO | 2005082436 A1 | 9/2005 |
| WO | 05110601 A1 | 11/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008094249 A1 | 8/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

Kohdaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

Anonymous: "Fuzzy control system", Wikipedia, Jan. 10, 2020. URL: https://en.wikipedia.org/w/index.php?title=Fuzzy_conlrol_system&oldid=935091190.

International Search Report and Written Opinion for the International Patent Application No. PCT/US2021/022694, dated Jun. 25, 2021, 13 pages.

Unger, Jeff, et al., "Glucose Control in the Hospitalized Patient," Emerg. Med 36(9):12-18 (2004).

Glucommander FAQ downloaded from https://adaendo.com/GlucommanderFAQ.html on Mar. 16, 2009.

Finfer, Simon & Heritier, Stephane. (2009). The Nice-Sugar (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation Nov. 16, 2003.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Farkas et al. ""Single-Versus Triple-Lumen Central Catheter-Related Sepsis: A Prospective Randomized Study in a Critically Ill Population"" The American Journal of Medicine September 1992vol. 93 p. 277-282.

Davidson, Paul C., et al., A computer-directed intravenous insulin system shown to be safe, simple, and effective in 120,618 h of operation, Diabetes Care, vol. 28, No. 10, Oct. 2005, pp. 2418-2423.

International Search Report and Written Opinion for the International Patent Application No. PCT/US2021/016283, dated Jun. 2, 2021, 15 pages.

(56) References Cited

OTHER PUBLICATIONS

Gorke, A. "Microbial contamination of haemodialysis catheter connections." EDTNA/ERCA journal (English ed.) vol. 31,2 (2005): 79-84. doi:10.1111/j.1755-6686.2005.tb00399.x.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Templeton et al, "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 dated Jul. 16, 2010 (OPTIS. 247VPC).

International Search Report and Written Opinion in PCT/US2008/079641 (Optis.203VPC) dated Feb. 25, 2009.

Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 623-627, Feb. 1, 1998.

Billman et al.,"Clinical Performance of an in line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; Chest/127/5/May 2005.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2000.

International Preliminary Report on Patentability for the International Patent Application No. PCT/US2019/053603, dated Apr. 8, 2021, 9 pages.

International Search Report and Written Opinion for the International Patent Application No. PCT/US2019/053603, dated Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech,vol., Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Jul. 2020, pp. 2064-2072.

An Emilia Fushimi: "Artificial Pancreas: Evaluating the ARG Algorithm Without Meal Announcement", Journal of Diabetes Science and Technology Diabetes Technology Society, Mar. 22, 2019, pp. 1025-1043.

International Search Report and Written Opinion for the International Patent Application No. PCT/US2021/017441, dated May 25, 2021, 12 pages.

International Search Report and Written Opinion for the InternationalPatent Application No. PCT/US2021/017664, dated May 26, 2021, 16 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, dated May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, dated May 27, 2021, 16 pages.

International Search Report and Written Opinion for the International Patent Application No. PCT/US2020/065226, dated May 31, 2021, 18 pages.

International Search Report and Written Opinion for the International Patent Application No. PCT/US2021/017659, dated May 31, 2021, 13 pages.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

International Search Report and Written Opinion for the International Patent Application No. PCT/US2020/052125, dated Aug. 12, 2020, 15 pages.

International Search Report and Written Opinion for the International Patent Application No. PCT/US2020/050332, dated Sep. 12, 2020, 12 pages.

European Patent Office, "Notification of Transmittal of the ISR and the Written Opinion of the International Searching Authority, or the Declaration," in PCT Application No. PCT/GB2015/050248, dated Jun. 23, 2015, 12 pages.

European Search Report for the European Patent Application No. 21168591.2, dated Oct. 13, 2021, 04 pages.

International Search Report and Written Opinion for the International Patent Application No. PCT/US2021/041954, dated Oct. 25, 2021, 13 pages.

International Search Report and Written Opinion for the International Patent Application No. PCT/US2021/047771, dated Dec. 22, 2021, 11 pages.

International Search Report and Written Opinion for the International Patent Application No. PCT/US2021/052855, dated Dec. 22, 2021, 11 pages.

International Search Report and Written Opinion for the International Patent Application No. PCT/US2022/013470, dated May 6, 2022, 14 pages.

International Search Report and Written Opinion for the International Patent Application No. PCT/US2022/013473, dated May 6, 2022, 13 pages.

(56) References Cited

OTHER PUBLICATIONS

International Search Report and Written Opinion for the International Patent Application No. PCT/US2022/019079, dated Jun. 2, 2022, 14 pages.
International Search Report and Written Opinion for the International Patent Application No. PCT/US2022/018453, dated Jun. 2, 2022, 13 pages.
International Search Report and Written Opinion for the International Patent Application No. PCT/US22/018700, dated Jun. 7, 2022, 13 pages.
International Search Report and Written Opinion for the International Patent Application No. PCT/US22/019080, dated Jun. 7, 2022, 14 pages.
International Search Report and Written Opinion for the International Patent Application No. PCT/US22/019664, dated Jun. 7, 2022, 14 pages.
International Search Report and Written Opinion for the International Patent Application No. PCT/US21/060618, dated Mar. 21, 2022, 15 pages.
Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
International Search Report and Written Opinion for the International Patent Application No. PCT/US2022/012896, dated Apr. 22, 2022, 15 pages.
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, dated Dec. 13, 2017, 8 pages.
Van Heusden et al., "Control-Relevant Models for Glucose Control using a Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, dated May 16, 2017, 12 pages.
International Search Report and Written Opinion for the International Patent Application No. PCT/US2018/018901, dated Aug. 6, 2018, 12 pages.
International Search Report and Written Opinion for International Patent Application No. PCT/US2018/052467, dated Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.
"Read NFC Tags with an iPHone App on iOS 11", GoToTags, Sep. 11, 2017, web <https://gototags.com/blog/read-nfc-tags-with-an-iphone-app-on-ios-11/>. (Year:2017).
International Search Report and Written Opinion for International Patent Application No. PCT/US2016/063350, dated Mar. 27, 2017, 9 pages.
Extended Search Report dated Aug. 13, 2018, issued in European Patent Application No. 16753053.4, 9 pages.
International Search Report and Written Opinion for International Patent Application No. PCT/US16/18452, dated Apr. 29, 2015, 9 pages.
International Preliminary Report on Patentability dated Aug. 31, 2017, issued in PCT Patent Application No. PCT/US2016/018452, 7 pages.
International Search Report and Written Opinion for International Patent Application No. PCT/US2019/055862, dated Mar. 11, 2020.
International Search Report and Written Opinion for Application No. PCT/US2019/030652, dated Sep. 25, 2019, 19 pages.
International Search Report and Written Opinion for International Patent Application No. PCT/US2021/051027, dated Jan. 7, 2022, 16 pages.
International Search Report and Written Opinion for International Patent Application No. PCT/US2021/052372, dated Jan. 26, 2022, 15 pages.
International Search Report and Written Opinion for the International Patent Application No. PCT/US2021/046607, dated Jan. 31, 2022, 20 pages.
International Search Report and Written Opinion for the International Patent Application No. PCT/US2021/055745, dated Feb. 14, 2022, 13 pages.

\* cited by examiner

PREDICTION OF MEAL AND/OR EXERCISE EVENTS BASED ON PERSISTENT RESIDUALS

CROSS-REFERENCE TO RELATED APPLICATIONS

This application claims the benefit of the filing date of U.S. Provisional Application Ser. No. 62/957,620, filed Jan. 6, 2020, the entire contents of which are incorporated herein by reference in their entirety.

BACKGROUND

Patients with type 1 diabetes may be treated with insulin deliveries in a number of different ways. One approach is to manually deliver a correction bolus of insulin to patients as needed. For instance, if a patient's blood glucose level is 170 mg/dL and the target blood glucose level is 120 mg/dL, a bolus of 1 U may be manually delivered to the patient (assuming a correction factor of 1:50). There are some potential problems with manually delivering such boluses to the patient. The patients may deliver improper amounts of insulin in the bolus. For instance, the user may need a significantly lower amount of insulin than the bolus amount of 1 U. The insulin that has been delivered cannot be taken back from the patient's bloodstream. As a result, the delivery of the bolus may put the patient at risk of hypoglycemia.

Another approach is for the insulin to be delivered automatically by an insulin pump system. This approach may overcome some of the problems with manual delivery of insulin boluses. The insulin pump systems may use a closed loop control system for regulating the amount of insulin delivered at fixed intervals, such as every 5 minutes. The closed loop algorithms used by the control system may employ a penalty for large insulin deliveries that is balanced in a cost function with a penalty for glucose level excursions. The use of the cost function typically results in smaller insulin deliveries that are delivered more frequently than the manually delivered boluses. The closed loop system may reassess a patient's need more often than a manual approach. These systems, however, may be error prone and may not account for all relevant factors.

SUMMARY

In accordance with an exemplary embodiment, a method is performed by a processor. Per the method, an actual blood glucose concentration history for a user is obtained. The actual blood glucose concentration history contains actual blood glucose concentration values and indications of when the actual blood glucose concentration values were obtained. A predicted blood glucose concentration history for the user is obtained. The predicted blood glucose concentration history contains predicted blood glucose concentration values and indications of when the predicted blood glucose concentration values were obtained. The predicted blood glucose concentration values in the blood glucose concentration history are generated using a model of glucose and insulin interactions. Residual values are calculated between values in the actual blood concentration history with like times in the predicted blood glucose concentration history over a time window. A rate of change of the residual values for groups of residual values for consecutive times in the time window is calculated. At least one calculated rate of change of the residual values for at least one of the groups is identified as having a magnitude that exceeds a threshold and that is positive. Based on the identifying, it is determined that the user has ingested a meal, and it is designating in the model that a meal was ingested by the user.

The method may further include delivering insulin to the user in response to designation of the meal event. The method may include delivering a bolus of insulin via drug delivery device. The delivering may comprise delivering a larger dosage of insulin during a basal insulin delivery. The threshold may be tailored to the insulin sensitivity of the user. The threshold may be set based on an empirical blood glucose response of the user to ingesting a meal.

In accordance with an exemplary embodiment, a method is performed by a processor. An actual blood glucose concentration history for a user is obtained. The actual blood glucose concentration history contains actual blood glucose concentration values and indications of when the actual blood glucose concentration values were obtained. Predicted blood glucose concentration history for the user is obtained. The predicted blood glucose concentration history contains predicted blood glucose concentration values and indications of when the predicted blood glucose concentration values were obtained. The predicted blood glucose concentration values in the blood glucose concentration history are generated by a model of glucose and insulin interactions. Residual values are calculated between values in the actual blood concentration history with like times in the predicted blood glucose concentration history over a time window. A rate of change of the residual values for groups of residual values for consecutive time times in the time window is calculated. At least one calculated rate of change of the residual values for at least one of the groups is identified as having a magnitude that exceeds a negative threshold and that is negative. Based on the identifying, it is determined that the user has exercised, and an exercise event by the user is designated in the model.

The method may further entail suspending basal delivery of insulin to the user from a drug delivery device in response to the designation of an exercise event. The drug delivery device may be a wearable insulin pump. The method may further entail reducing a basal delivery dosage of insulin from a drug delivery device in response to the designation of an exercise event. The threshold may be tailored to the user. The threshold may be based on empirical blood glucose concentration response of the user to exercise.

In accordance with an exemplary embodiment, a device for controlling delivery of insulin to a user via a drug delivery device includes a storage for storing an actual blood glucose concentration history for a user, a predicted blood glucose concentration history for the user, a model of glucose insulin interactions for the user and a control application for controlling a drug delivery device for delivering insulin to the user. The actual blood glucose concentration history contains actual blood glucose concentration values and indications of when the actual blood glucose concentration values were obtained, and the predicted blood glucose concentration history contains predicted blood glucose concentration values and indications of when the predicted blood glucose concentration values were obtained. The predicted blood glucose concentration values in the blood glucose concentration history are generated by the model of glucose and insulin interactions. The device also includes a processor for executing instructions causing the processor to calculate residual values between values in the actual blood concentration history with like times in the predicted blood glucose concentration history over a time window. The instructions also cause the processor to calculate a rate of change of the residual values for groups of residual values for consecutive time times in the time window and identify at least one calculated rate of change of the residual values for at least one of the groups that has a magnitude that exceeds a positive threshold and that is positive or identify at least one calculated rate of change of the residual values for at least one of the groups that has a magnitude that exceeds a negative threshold and that is negative. Where it is identified that at least one calculated rate of change of the residual values for at least one of the groups has a magnitude that exceeds the positive threshold and is positive, it is determined that the user has ingested a meal, and a meal event by the user is designated in the model. Where it is identified that at least one calculated rate of change of the residual values for at least one of the groups has a magnitude that exceeds the negative threshold and is negative, it is determined that the user has exercised, and an exercise event by the user is designated in the model.

The processor may also cause remedial measures to be taken by the drug delivery device in response to designating a meal event or an exercise event. The remedial measures may comprise at least one of delivering a bolus of insulin to the user, increasing dosage of a basal insulin delivered to the user, suspending delivery of insulin to the user or decreasing dosage of a basal insulin delivered to the user. At least one of the positive threshold or the negative threshold may be customized to the user. The device may be an insulin pump device or the device may be a separate device that controls an insulin pump device.

DETAILED DESCRIPTION

The exemplary embodiments address some of the limitations of some conventional insulin delivery system control systems. Exemplary embodiments provide an approach to predicting meal and/or exercise events for an insulin delivery system that otherwise does not otherwise identify such events. The insulin delivery system may use a model of glucose insulin interactions that projects estimated future glucose values based on the history of glucose values and insulin deliveries for the user. The predictions of meal events and/or exercise events may be based on residuals between actual glucose values and predicted glucose values. The exemplary embodiments may calculate a rate of change of the residuals over a period of time (such as over a fifteen minute period) and compare the rate of change to thresholds to determine whether there likely has been a meal event or an exercise event. For instance, if the rate of change is positive and the rate is above a first threshold, it is indicative of a meal event, and such a meal event may be designated. On the other hand, if the rate of change is negative and the rate of change is below a second threshold, it is indicative of an exercise event, and such an event may be designated. The drug delivery system may then take measures to account for the meal or exercise by the user.

Figure 1:
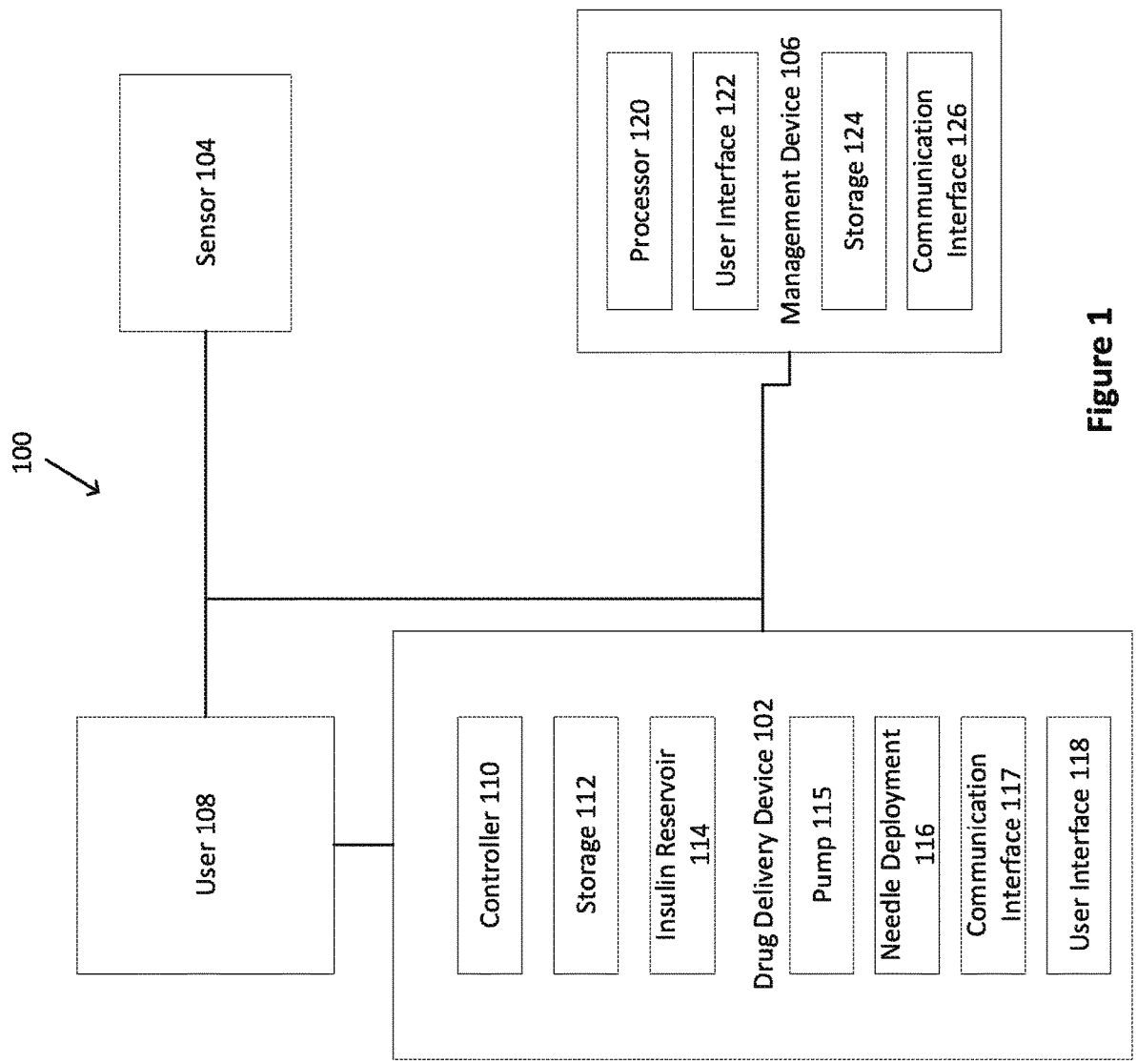
FIG. 1 depicts a block diagram of an illustrative drug delivery system suitable for practicing an exemplary embodiment.

FIG. 1 depicts an illustrative drug delivery system 100 that is suitable for delivering insulin to the user 108 in an exemplary embodiment. The drug delivery system 100 includes a drug delivery device 102. The drug delivery device 102 may be a wearable device that is worn on the body of the user 108. The drug delivery device 102 may be directly coupled to the user 108 (e.g., directly attached to a body part and/or skin of the user 108 via an adhesive or the like). In an example, a surface of the drug delivery device 102 may include an adhesive to facilitate attachment to the user 108.

The drug delivery device 102 may include a controller 110. The controller 110 may be implemented in hardware, software, or any combination thereof. The controller 110 may, for example, be a microprocessor, a logic circuit, a field programmable gate array (FPGA), an application specific integrated circuit (ASIC) or a microcontroller coupled to a memory. The controller 110 may maintain a date and time as well as other functions (e.g., calculations or the like). The controller 110 may be operable to execute an algorithm stored in the storage 112 that enables the controller 110 to direct operation of the drug delivery device 102. In addition, the controller 110 may be operable to receive data or information. The storage 112 may include both primary memory and secondary memory. The storage 112 may include random access memory (RAM), read only memory (ROM), optical storage, magnetic storage, removable storage media, solid state storage or the like.

The drug delivery device 102 may include an insulin reservoir 114 for storing insulin for delivery to the user 108 as warranted. A pump 115 may be provided for pumping the insulin out of the insulin reservoir 114 to the user 108. A needle deployment component 116 may be provided to control deployment of needles or cannulas from the drug delivery device 102 to the user 108. The needle deployment component 116 may, for example, include a needle, a cannula and/or any other fluid path components for coupling the stored liquid drug in the insulin reservoir 114 to the user 108. The cannula may form a portion of the fluid path component coupling the user to the insulin reservoir 114. After the needle deployment component 116 has been activated, a fluid path to the user is provided, and the pump 115 may expel the liquid drug from the reservoir 114 to deliver the liquid drug to the user via the fluid path. The fluid path may, for example, include tubing coupling the drug delivery device 102 to the user 108 (e.g., tubing coupling the cannula to the reservoir 114).

The communications interface 117 may provide a communications link to one or more management devices physically separated from the drug delivery device 102 including, for example, a management device 104 of the user and/or a caregiver of the user. The communication link provided by the communications interface 117 may include any wired or wireless communication link operating according to any known communications protocol or standard, such as Bluetooth®, Wi-Fi, a near-field communication standard, a cellular standard, or any other wireless protocol. The drug delivery device 102 may also include a user interface 118, such as an integrated display device for displaying information to the user 108 and in some embodiments, receiving information from the user 108. The user interface 118 may include a touchscreen and/or one or more input devices, such as buttons, knob or a keyboard.

The drug delivery system 100 may include a sensor 104 for sensing the blood glucose concentration levels of the user 108. The sensor 104 may be a glucose monitor that provides periodic blood glucose concentration measurements, such as a continuous glucose monitor (CGM), or another type of device or sensor that provides blood glucose measurements. The sensor 104 may be physically separate from the drug delivery device 102 or may be an integrated component thereof. The sensor 104 may provide the controller 110 with data indicative of measured or detected blood glucose levels of the user 108. The sensor 104 may be coupled to the user by, for example, adhesive or the like and may provide information or data on one or more medical conditions and/or physical attributes of the user 108. The information or data provided by the sensor 104 may be used to adjust drug delivery operations of the drug delivery device 102.

The drug delivery system 100 may also include the management device 106. The management device 106 may be a special purpose device, such as a personal diabetes manager (PDM). The management device 106 may be a programmed general purpose device, such as any portable electronic device including, for example, a dedicated controller, such as processor, a smartphone, or a tablet. The management device 106 may be used to program or adjust operation of the drug delivery device 102 and/or the sensor 104. The management device 106 may be any portable electronic device including, for example, a dedicated controller, a smartphone, or a tablet. In the depicted example, the management device 106 may include a processor 120, a storage 124, and a communication interface 126. Processor 120 may execute processes to manage a user's blood glucose levels and for control the delivery of the drug or therapeutic agent to the user 108. The processor 120 may also be operable to execute programming code stored in the management storage 124. For example, the storage may be operable to store one or more control applications for execution by the processor 120. The communication interface 126 may include a receiver, a transmitter, or a transceiver that operates according to one or more radio-frequency protocols. For example, the communication interface 126 may include a cellular transceiver and a Bluetooth transceiver that enables the management device 106 to communicate with a data network via the cellular transceiver and with the sensor 104 and the drug delivery device 102. The respective transceivers of communication interface 126 may be operable to transmit signals containing information useable by or generated by an application or the like. The communication interfaces 117 and 126 of respective wearable drug delivery device 102 and sensor 104, respectively, may also be operable to transmit signals containing information useable by or generated by an application or the like.

The management device 106 may include a user interface 122 for communicating with the user 108. The user interface 122 may include a display, such as a touchscreen, for displaying information. The touchscreen may also be used to receive input when it is a touch screen. The user interface 122 may also include input elements, such as a keyboard, button, knobs or the like.

Figure 2:
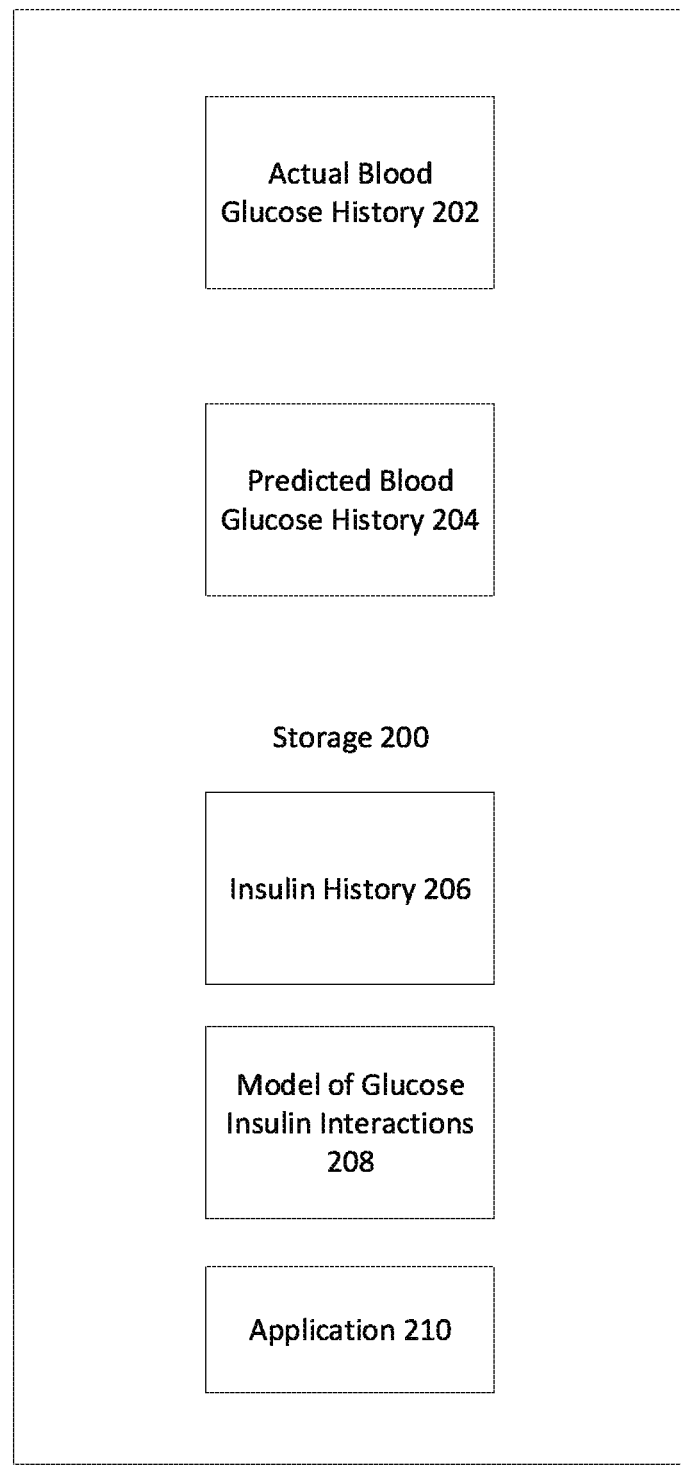
FIG. 2 depicts contents of an illustrative storage for use in the drug delivery system.

FIG. 2 shows an example of contents held in a storage 200, such as storage 112 of the drug delivery device or storage 124 of the management device 106. The storage 200 may hold the actual blood glucose history 202, which contains the history of blood glucose concentration readings from the sensor 104 for the user 108 over time. The storage 200 may hold the predicted blood glucose history containing the predicted blood glucose values for the user 108 generated by the model used in the drug delivery system. This model 108 may be encoded in application 210 that is executed by the controller 110 with input from the management device 106 and sensor 104. The application 210 may be executed to control the drug delivery device 102 and oversee activities of the drug delivery device 102. The storage 200 may also store the insulin history 206 that records the insulin deliveries and delivery times and/or cycles for the user 108.

Figure 3:
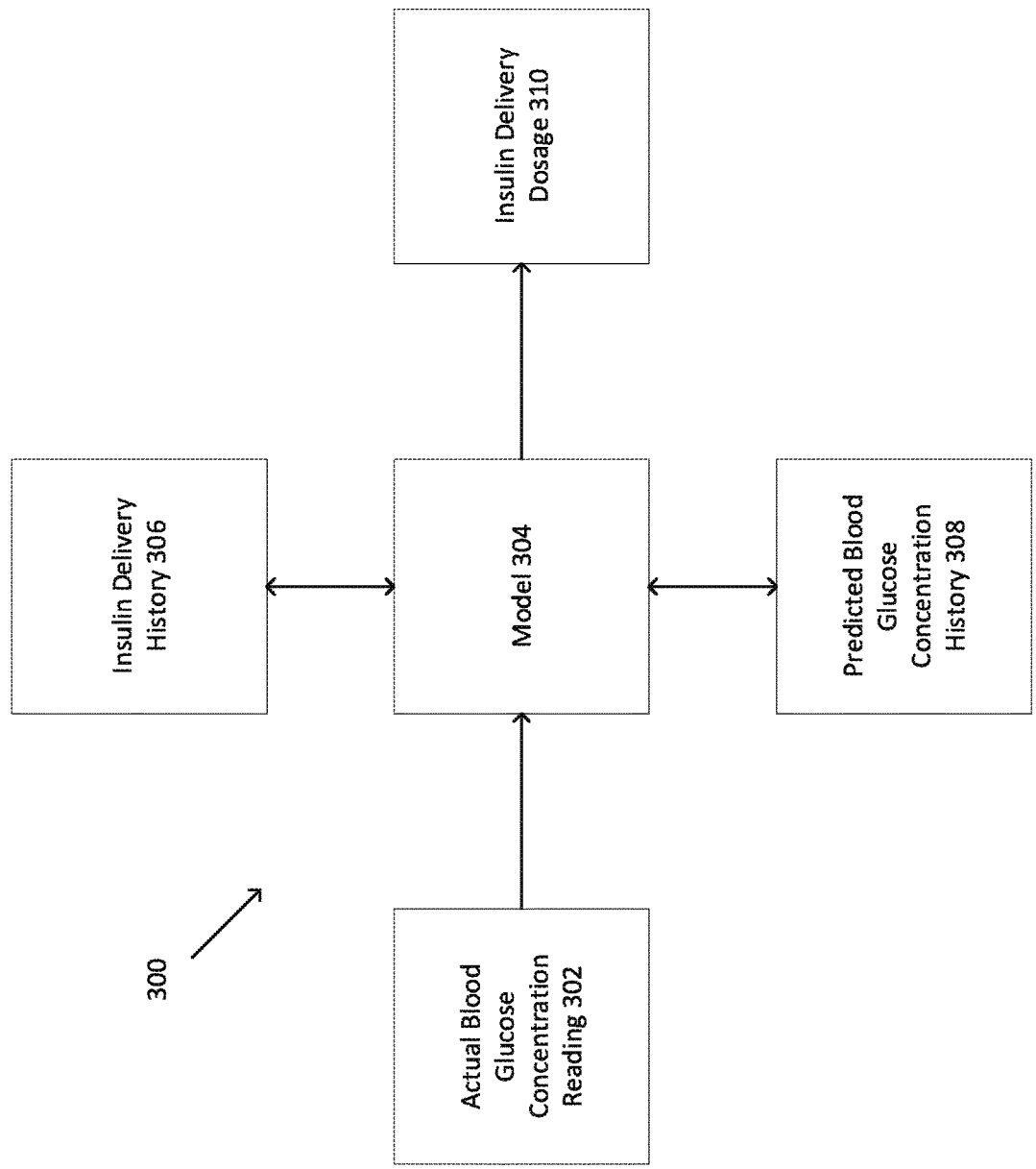
FIG. 3 illustrates a block diagram showing inputs and output of a glucose insulin interaction model.

FIG. 3 depicts a block diagram 300 showing input and outputs of the model 304 of glucose/insulin interactions that is used by the application 210 in managing the drug delivery device 102. The model 304 receives the actual blood glucose concentration reading 302 from the sensor 104. The actual blood glucose concentration readings may be delivered at periodic intervals, such as cycles of every 5 minutes, in some embodiments. The actual blood glucose concentration in compared to the predicted blood glucose concentration for the same time in the predicted blood glucose concentration history 308. The model 304 predicts blood glucose concentration at times. The predictions are used to determine and control the system response to actual blood glucose concentrations. The predicted blood glucose concentration history 308 holds the values predicted by the model 304 over time. The model 304 also looks at the insulin delivery history 306 for the user. The insulin delivery history 306 contains the dosages and times and/or cycles of all bolus insulin deliveries and basal insulin deliveries to the user. Based on the inputs 302, 306 and 308, the model 304 generates an output control signal to the pump 115 that specifies an insulin delivery dosage 310 if warranted. The dosage may be zero, in which case no insulin is to be delivered. The model 304 may seek to deliver small dosages rather than larger boluses to avoid hypoglycemic or hyperglycemic risks. Moreover, the model 304 may account for other parameters that affect blood glucose concentration levels.

As was mentioned above, the exemplary embodiments embellish the model 304 to account for meals by the user and exercise by the user. The exemplary embodiments may identify meals or exercise by looking at residuals between the actual blood glucose concentration values for the user and predicted blood glucose concentration values. The difference between the actual values and the predicted values provide a magnitude of error for the predictions. Such error may come from multiple sources. In order to identify the error as originating from an unaccounted meal or exercise, the exemplary embodiments may look for significant enough residuals that change substantially between successive readings in a time interval. For example, when a user ingests a meal, the blood glucose concentration for the user will increase fairly rapidly after ingestion and will continue to increase as the remaining portions of the meal are digested.

The predicted blood glucose level will not anticipate such an increase in blood glucose concentration. Thus, a rapid increase in the residuals is indicative of the user ingesting a meal. When a user exercises, the blood glucose concentration level will drop fairly rapidly until the user stops exercising. The predicted blood glucose level will not anticipate such a decrease in blood glucose concentration level. Hence, the rate of change of the residuals also may be indicative of exercise in some instances.

Figure 4:
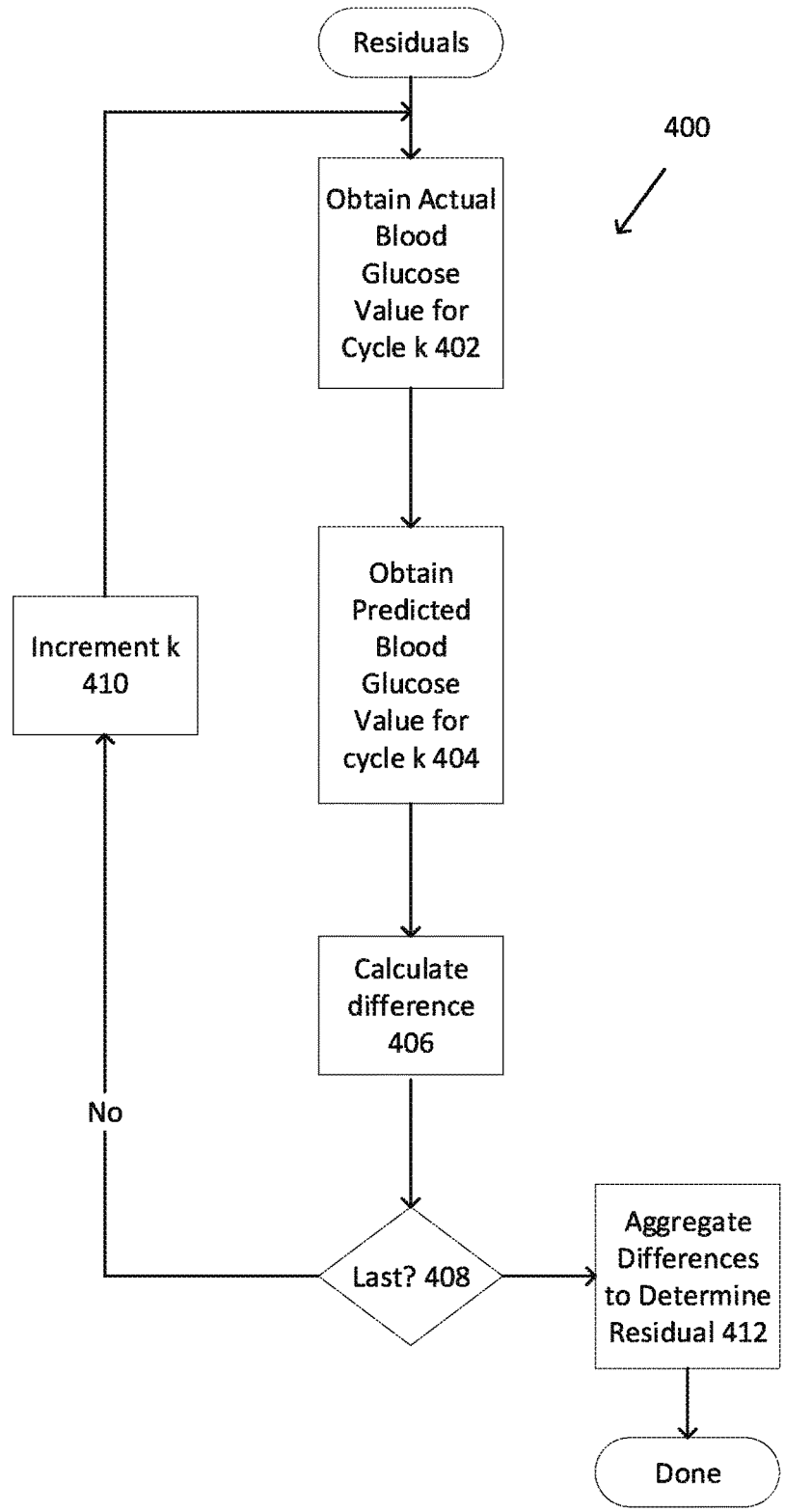
FIG. 4 depicts a flowchart showing illustrative steps for determining residuals between actual blood glucose concentration values and predicted blood glucose concentration values.

FIG. 4 depicts a flowchart 400 shows illustrative steps for determining residuals over time. First, the actual blood glucose concentration level for cycle k is determined (402), where k is a positive integer that serves as a cycle index value. The drug delivery system 100 may be configured to operate in periodic cycles, such as at 5 minute intervals, where the newest actual blood glucose concentration value is obtained and insulin deliveries may be made based on the latest value. This may be the value provided by the sensor 104 at cycle k. The predicted blood glucose concentration level at cycle k is also obtained (404). A recursive model of $n^{th}$ order may be used to project the future glucose values $G_p$. The future glucose values are predicted from the past blood glucose concentration values and insulin delivery values as:

$$G_p(k) = b_1 G(k-1) + b_2 G(k-2) + \ldots b_n G(k-n) + I(k-1) + I(k-2) + I(k-n)$$

Where $G_p(k)$ is the predicted glucose value at cycle k; G(k) is an actual blood glucose concentration value at cycle k; $b_x$ is a weight assigned to the past coefficient where x is an index value ranging from 1 to n; and I(k) is an insulin action for a dosage amount (i.e., how much the dosage of insulin will reduce the blood glucose concentration) delivered at cycle k.

The difference for cycle k may be calculated by subtracting the predicted blood glucose concentration value from the actual blood glucose concentration value (406). If this is the last cycle of interest (see 408), then the process is complete. If not, the cycle index is incremented (410) and the process is repeated beginning at (402).

The prediction residual for each cycle may be calculated by comparing the actual blood glucose concentration values to the predicted blood glucose concentration values over cycles k to k+m and summing those differences (412) as follows:

$$R(k+m) = \sum_{q=0}^{m} G(k+q) - G_p(k+q)$$

Where R(k+m) is the residual for the cycle k+m; and q is an index ranging from 0 to m.

Figure 5:
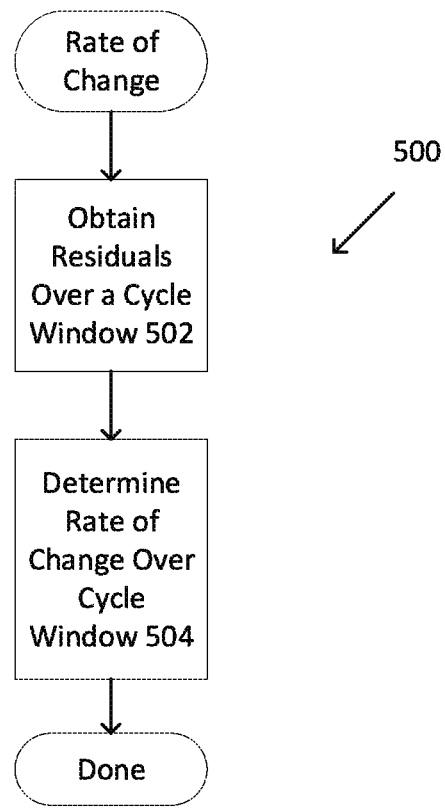
FIG. 5 depicts a flowchart showing illustrative steps for determining a rate of change of residual values for a cycle.

As was mentioned above, it is not the residuals for successive cycles alone that are or interest but rather the rate of change of the residuals over multiple successive cycles that is of interest. FIG. 5 shows a flowchart 500 of how the rate of change of the residuals is determined. Initially, the residuals over a window of successive cycles are obtained (502). In one exemplary case, the residuals for 3 successive cycles may be obtained in an exemplary case. The residuals for each cycle may be calculated using the summation set forth above. The rate of change of the residuals is then determined (504). This may be calculated by calculating the difference between the first and last residuals in a group of three successive cycles and dividing the sum by the number of cycles. If three cycles constitute the time window of instance, the rate of change may be expressed as:

$$ROC_3(k+m) = \frac{R(k+m) - R(k+m-2)}{3}$$

Where $ROC_3(k+m)$ is the rate of change of the residual over three successive cycles spanning cycles k through m and R(i) is the residual for cycle i.

Figure 6A:
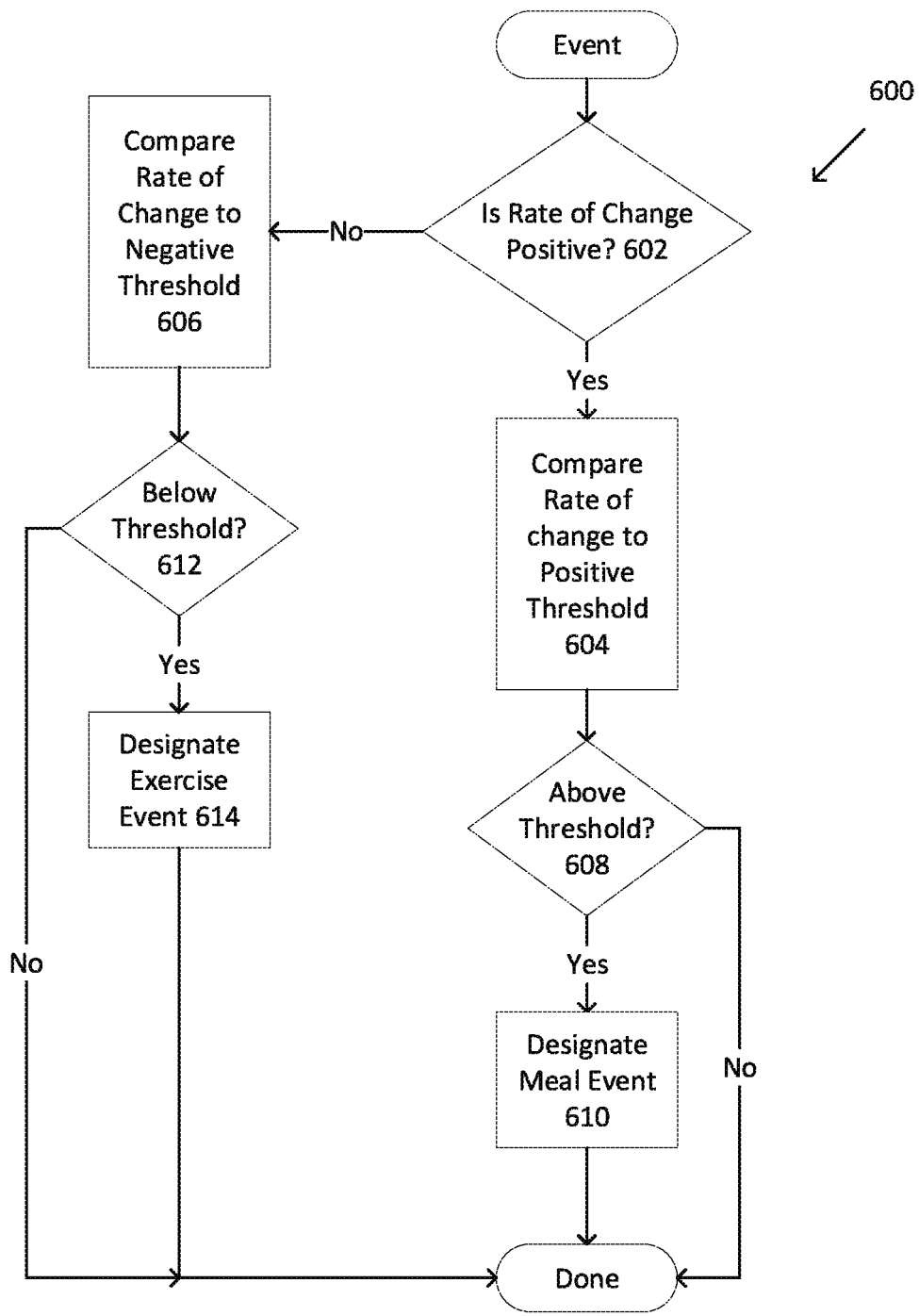
FIG. 6A depicts a flowchart showing illustrative steps for determining when to designate a meal event or an exercise event.

The rates of change of the residuals may then be analyzed to identify meal events or exercise events. FIG. 6A depicts a flowchart 600 showing illustrative steps for determining such events. A check may be made whether the rate of change of the residuals in positive (602). If the rate of change is positive, it implies that the actual blood glucose concentration values are increasing more rapidly than the predicted blood glucose concentration values. The rate of change is compared to a positive threshold (604). The comparison to the positive threshold helps to rule out rates of change that are not as substantial as would be evidenced by a meal. If the rate of change is above the positive threshold (608), a meal event is designated (610). If the rate of change is not positive (see 602), the rate of change may be compared with a negative threshold (606). If the rate of change is below the negative threshold (i.e., more negative than the threshold) (612), an exercise event may be designated (614). Otherwise, no event is designated.

The positive threshold for determining meal events and the negative threshold for determining exercise events may be customized for the user. For example, data may be gathered for the user for actual meal events and the residuals and residual rate of change may be calculated for those actual meal events. Based on the actual data, the positive threshold may be set to distinguish meal events from other phenomena. Similarly, empirical data regarding actual exercise events concerning the residuals and the rate of change of the residuals for actual exercise events may be used to set the negative threshold.

Multiple thresholds can also be generated to define different degrees or types of meal events and exercise events. For example, the magnitudes of residuals and residual rate of change can be varying in tandem or independently depending on the type of a meal, where a slow absorbing meal may exhibit a slower increase in glucose and thus a smaller residual versus a fast-absorbing meal. A larger meal of the same type may simply exhibit a similar error for a longer period, and the residual threshold can be set higher if the goal is to detect larger meals only. Similarly, a fast-absorbing meal may exhibit a temporarily rapid increase in glucose, and thus the residual rate of change threshold can also be set higher to detect such a meal. Similarly, aerobic and anaerobic exercises can exhibit different patterns of residuals versus predictions. Short, intense bouts of exercise may indicate high rates of change but not a significant increase in thresholds, while leisurely, longer acting activities may result in lower rates of change but persistent increases over time. Therefore, the combination of residual thresholds and residual rate of change thresholds can be tuned differently, or tuned for multiple instances, to allow for detection of both event types and different degrees of meals and exercise.

Figure 6B:
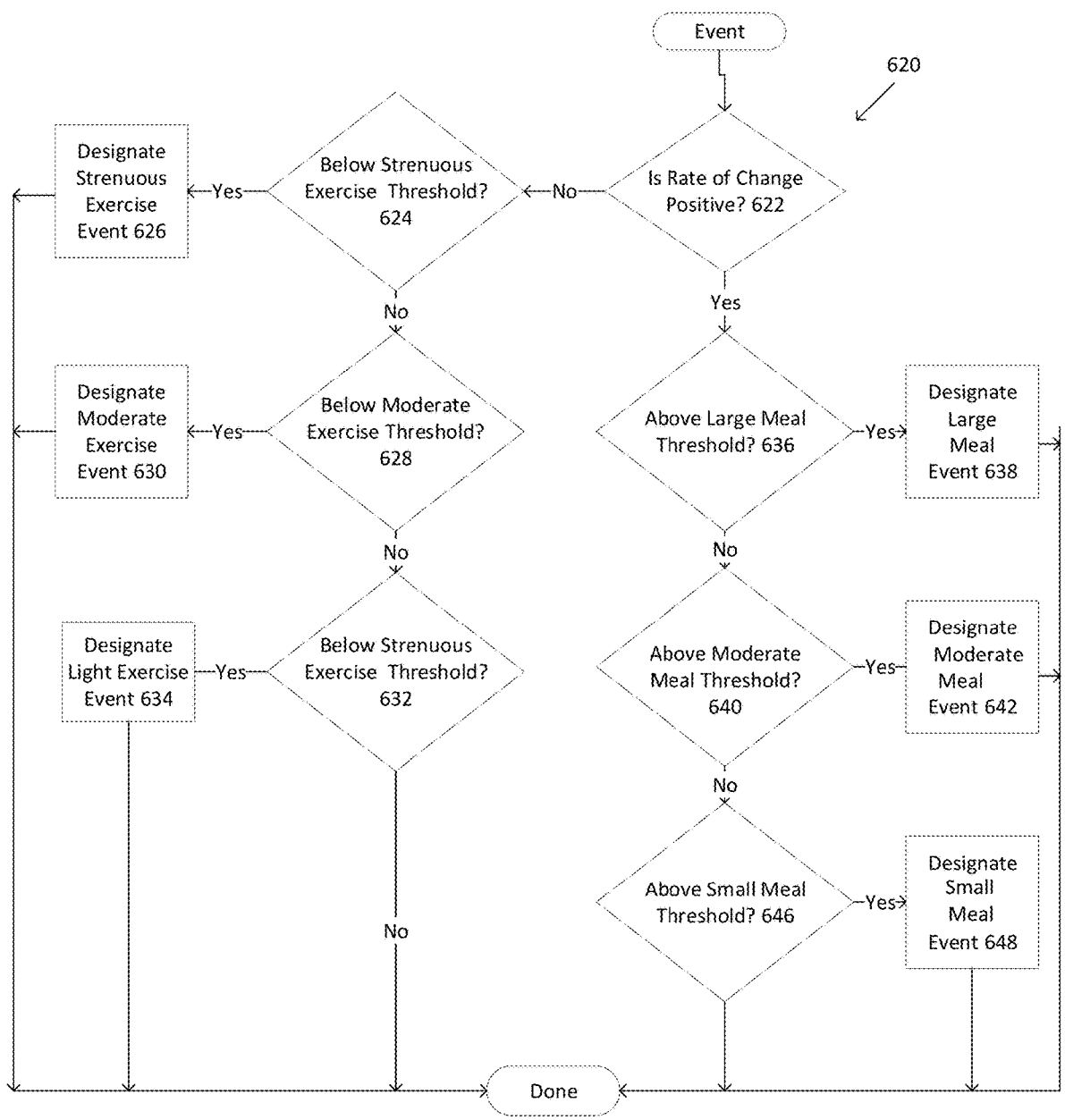
FIG. 6B depicts a flowchart showing illustrative steps for determining when to designate different types of meal events and different types of exercise events.

FIG. 6B depicts a flowchart showing illustrative steps that may be performed to designate different types of meal events and/or different types of exercise events for an illustrative case. In this instance, the rate of change of the residual dictates the designation and categorization of exercise and meal events. First, a check in made whether the rate of change of the residuals in positive or negative (622). If the rate of change is negative, it may be an indication that the user is exercising. Hence, a check is made whether the rate of change is below (i.e., more negative) than a strenuous exercise threshold (624). If the rate of change is below the strenuous exercise threshold, a strenuous exercise event is designated (626). If not, a check is made whether the rate of change is below a moderate exercise threshold (628). If the rate of change is below the moderate exercise threshold, a moderate exercise threshold event is designated (630). If the rate of change is not below the moderate exercise threshold, a check is made whether the rate of change is below a light exercise threshold (632). If the rate of change is below the light exercise threshold, a light exercise event is designated (634). Otherwise, no exercise event is designated.

If it is determined that the rate of change is positive (see 622), it may be an indication that the user has eaten. A check is made whether the rate of change is greater than a large meal threshold (636). If so, a large meal event is designated (638). If not, a check is made whether the rate of change is above a moderate meal threshold (640). If so, a moderate meal event is designated (642). If not, a check is made whether the rate of change is above a small meal threshold (646). If so, a small meal event is designated (648). If not, no meal event is designated.

Figure 6C:
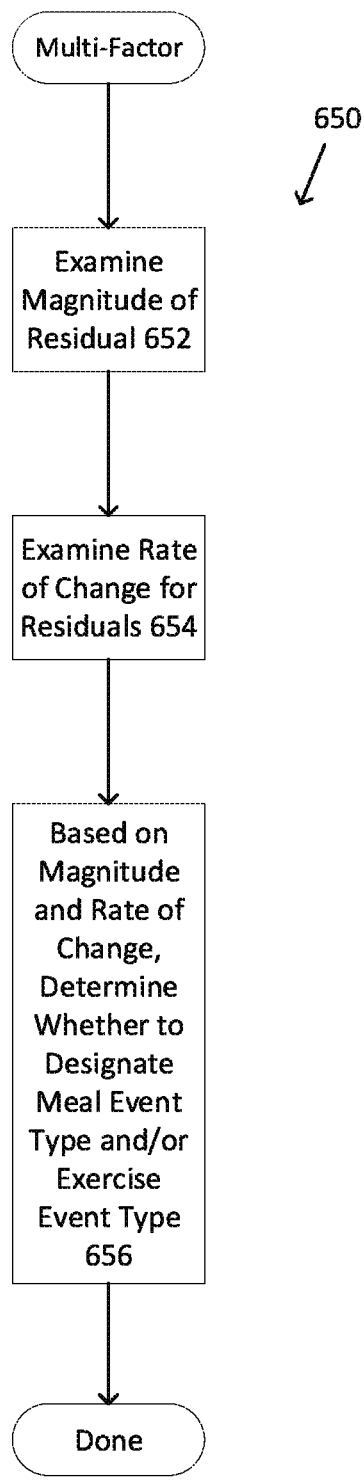
FIG. 6C depicts a flowchart showing illustrative steps that may be performed when both magnitude of a residual and rate of change of residuals are used to determine whether to designate a meal event type or an exercise event type.

In another variant, as mentioned above, both the magnitude of the residual and the rate of change of the residual may be used to determine meal or exercise event designations of different degrees. FIG. 6C depicts a flowchart (650) of illustrative steps that may be performed for this variant. The process may entail examining the magnitude of the residual (e.g., the current residual) (652). The rate of change of the residuals (e.g., the latest rate of change) is examined as well (654). Based on both the magnitude of the residual and the rate of change of the residual, a determination is made whether to designate a meal event of a given degree or an exercise event type of a given degree (656). As mentioned above, combinations of thresholds may be used to make this determination and cause a designation as warranted.

Another approach is to relate a user's total insulin delivery (TDI) for a day and relate it to the user's insulin to carbohydrate ratio that identifies how much insulin is required to offset a specified amount of carbohydrates. These values may be related by heuristic rules, such as the 800 rule, which looks at 800/TDI to determine the ratio of a carbohydrate ingestion amount that may be offset by 1 unit of insulin. The correction factor may specify how much of a drop in glucose is realized by one unit of insulin, through heuristics such as the 1800 rule (1800/TDI). A combination of these rules can be utilized to estimate the quantity and presence of the user's events. For instance, it may be desired that the system would detect a meal event with carbohydrate quantity above a certain threshold, such as 30 grams. These 30 grams of carbohydrates can be converted into the estimated amount of insulin that would be needed to compensate for the event. If the user's TDI is 50 U, then the 800 rule (800/TDI) means 1 U of insulin would compensate for 16 g, and the 30 grams of carbohydrates require 1.875 U of insulin. This can also be correlated to expected glucose rise, based on the user's correction factor, which through the 1800 rule (1800/TDI) would mean 1 U of insulin reduces glucose by 36 mg/dL, and 1.875 U of insulin would reduce insulin by 67.5 mg/dL. Therefore, the threshold can be designed in such a way that an unexpected rise in glucose rise by more than 67.5 mg/dL would be detected.

Figure 7:
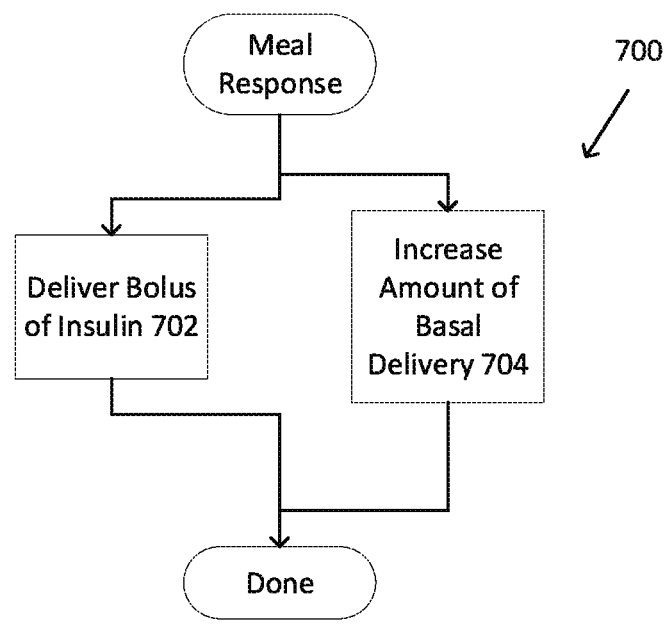
FIG. 7 depicts a flowchart showing illustrative steps for responding to a meal event.

The drug delivery system 100 may respond to the designation of a meal event and/or an exercise event. FIG. 7 depicts a flowchart 700 showing illustrative steps that may be performed in response a meal event being designated. Since, a meal event indicates that the user has ingested food that has raised the actual blood glucose concentration level of the user, the drug delivery system 100 may take steps to reduce the blood glucose concentration level of the user. For instance, a bolus of insulin may be delivered to the user (702). Another option is to increase the dosage of the basal insulin delivery (704). These options may be done automatically by the controller 110 which is executing the application for controlling the drug delivery device 102. The steps 702 and 704 may be realized by loosening constraints in the model to allow greater insulin delivery.

Figure 8:
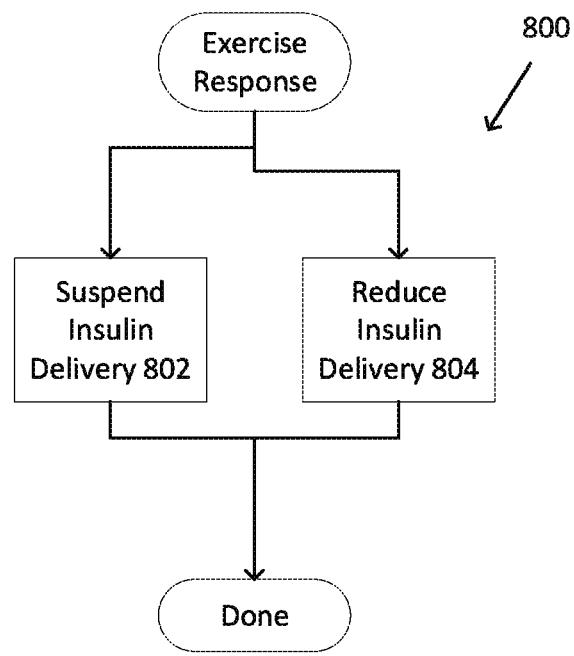
FIG. 8 depicts a flowchart showing illustrative steps for responding to an exercise event.

FIG. 8 depicts a flowchart 800 showing illustrative steps that may performed in response to the designation of an exercise event. Exercise will reduce the blood glucose concentration level of the user. Thus, the aim is to take steps to avoid further decreases in the blood glucose concentration level of the user. One option is to halt deliveries of basal insulin to the user for a specified period of time (802). Another option is to decrease the dosage level of the automatically delivered insulin (804). These options may be done automatically by the controller 110 which is executing the application for controlling the drug delivery device 102. The constraints in the model may be adjusted to suspend or decrease the insulin delivery in (802) and (804).

In an alternative embodiment, the values of the residuals are not used; rather the summed square of the residuals are used. The summed square of residuals $R_{SSR}$ can be expressed as an extension to the equation in 0031 where $$R_{SSR}(k+m) = \sum_{q=0}^{m}(G(k+q) - G_p(k+q))^2$$

This helps to reduce the effect of outliers using the previously described approach. The signs of the residuals must be maintained as the squaring will make all the squares positive. One option is to set all of the residuals of an undesired sign (i.e., the sign not of interest when comparing to a particular threshold) to zero.

While the present invention has been described with reference to exemplary embodiments thereof, it should be appreciated that various changes in form and/or detail may be made without departing from the intended scope of the present invention as defined in the appended claims. For example, the residuals may also be used to identify other unknown system events, such as error produced by pressure-induced sensor attenuation. Pressure-induced sensor attenuations may result in sudden reduction in glucose concentrations similar to immediate glucose outcomes following exercise events, and may be detected in a similar manner by observing sudden unexpected accumulation of negative residual values versus predictions.

The invention claimed is:

1. A method performed by a processor, comprising:
obtaining an actual glucose concentration history for a user, the actual glucose concentration history containing actual glucose concentration values and indications of when the actual glucose concentration values were obtained;
obtaining a predicted glucose concentration history for the user, wherein the predicted glucose concentration history contains predicted glucose concentration values and indications of when the predicted glucose concentration values were obtained and wherein the predicted glucose concentration values in the predicted glucose concentration history were generated using a model of glucose and insulin interactions;

calculating residual values between the actual glucose concentration values and the predicted glucose concentration values at like times over a time window;

calculating a rate of change of the residual values for groups of the residual values for consecutive times in the time window;

identifying at least one calculated rate of change of the residual values for at least one of the groups that has a magnitude that surpasses a threshold; and based on the identifying, determining that the user has either (a) ingested a meal and designating a meal event indicating that the meal was ingested by the user in the model without the user providing an indication that the meal was ingested or (b) exercised and designating an exercise event indicating that the user has exercised in the model without the user providing an indication that the user has exercised.

2. The method of claim 1, wherein the meal event has been designated and wherein the method further comprises delivering insulin to the user in response to the designation of the meal event.

3. The method of claim 2, wherein the delivering comprises delivering a bolus of the insulin via a drug delivery device.

4. The method of claim 2, wherein the delivering comprises delivering a dosage of the insulin during a basal insulin delivery.

5. The method of claim 1, wherein the threshold is tailored to an insulin sensitivity of the user.

6. The method of claim 1, wherein the threshold is set based on an empirical blood glucose response of the user to ingesting the meal.

7. The method of claim 1, wherein the exercise event was designated and wherein the method further comprises suspending basal delivery of insulin to the user from a drug delivery device in response to the designation of the exercise event.

8. The method of claim 7, wherein the drug delivery device is a wearable insulin pump.

9. The method of claim 7, wherein the threshold is based on an empirical glucose concentration response of the user to exercise.

10. The method of claim 1, further comprising reducing a basal delivery dosage of insulin from a drug delivery device in response to the designation of the exercise event.

11. A method performed by a processor, comprising:

obtaining an actual glucose concentration history for a user, the actual glucose concentration history containing actual glucose concentration values and indications of when the actual glucose concentration values were obtained;

obtaining a predicted glucose concentration history for the user, wherein the predicted glucose concentration history contains predicted glucose concentration values and indications of when the predicted glucose concentration values were obtained and wherein the predicted glucose concentration values in the predicted glucose concentration history were generated by a model of glucose and insulin interactions;

calculating residual values between the actual glucose concentration values and the predicted glucose concentration values at like times over a time window;

calculating a rate of change of the residual values for groups of the residual values for consecutive times in the time window;

identifying at least one calculated rate of change of the residual values for at least one of the groups that has a magnitude that exceeds a threshold; and based on the identifying, designating a user activity in the model without the user providing an indication that the user has engaged in the user activity.

\* \* \* \* \*